(12) United States Patent
Dimeo, Jr. et al.

(10) Patent No.: US 7,296,458 B2
(45) Date of Patent: *Nov. 20, 2007

(54) NICKEL-COATED FREE-STANDING SILICON CARBIDE STRUCTURE FOR SENSING FLUORO OR HALOGEN SPECIES IN SEMICONDUCTOR PROCESSING SYSTEMS, AND PROCESSES OF MAKING AND USING SAME

(75) Inventors: Frank Dimeo, Jr., Danbury, CT (US);
Philip S. H. Chen, Bethel, CT (US);
Ing-Shin Chen, Danbury, CT (US);
Jeffrey W. Neuner, Bethel, CT (US);
James Welch, New Fairfield, CT (US)

(73) Assignee: Advanced Technology Materials, Inc, Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/784,606

(22) Filed: Feb. 23, 2004

(65) Prior Publication Data

US 2004/0163444 A1 Aug. 26, 2004

Related U.S. Application Data

(63) Continuation-in-part of application No. 10/273,036, filed on Oct. 17, 2002.

(51) Int. Cl.
*G01N 7/00* (2006.01)
(52) U.S. Cl. .................. 73/23.2; 73/23.4; 73/31.06
(58) Field of Classification Search ............ 73/31.05, 73/31.06, 23.2, 23.02, 23.21, 23.22, 23.35; 436/144, 147; 422/83; 257/77
See application file for complete search history.

(56) References Cited

U.S. PATENT DOCUMENTS

| | | | |
|---|---|---|---|
| 3,676,293 A | * | 7/1972 | Gruber ............... 428/408 |
| 3,764,269 A | | 10/1973 | Oldham et al. |
| 3,999,947 A | | 12/1976 | Mihara et al. |
| 4,480,779 A | | 11/1984 | Luc |

(Continued)

FOREIGN PATENT DOCUMENTS

JP 01-094255 A1 4/1989

(Continued)

OTHER PUBLICATIONS

U.S. Appl. No. 10/273,036, filed Oct. 17, 2002, Frank DiMeo, Jr., et al.

(Continued)

*Primary Examiner*—Hezron E. Williams
*Assistant Examiner*—Jacques M. Saint-Surin
(74) *Attorney, Agent, or Firm*—Vincent K. Gustafson; Intellectual Property/Technology Law; Maggie Chappuis

(57) ABSTRACT

A (MEMS)-based gas sensor assembly for detecting a fluorine-containing species in a gas containing same, e.g., an effluent of a semiconductor processing tool undergoing etch cleaning with HF, $NF_3$, etc. Such gas sensor assembly in a preferred embodiment comprises a free-standing silicon carbide support structure having a layer of a gas sensing material, preferably nickel or nickel alloy, coated thereon. Such gas sensor assembly is preferably fabricated by micromolding techniques employing sacrificial molds that are subsequently removable for forming structure layers.

38 Claims, 5 Drawing Sheets

U.S. PATENT DOCUMENTS

| | | | |
|---|---|---|---|
| 4,723,438 A | 2/1988 | Adler-Golden et al. | |
| 4,872,759 A | 10/1989 | Stich-Baumeister et al. | |
| 5,072,262 A | 12/1991 | Uekita et al. | |
| 5,098,864 A | 3/1992 | Mahulikar | |
| 5,104,513 A | 4/1992 | Lee et al. | |
| 5,229,625 A * | 7/1993 | Suzuki et al. | 257/77 |
| 5,376,255 A | 12/1994 | Gumbrecht et al. | |
| 5,387,462 A | 2/1995 | Debe | |
| 5,434,551 A | 7/1995 | Chen et al. | |
| 5,464,966 A | 11/1995 | Gaitan et al. | |
| 5,602,051 A | 2/1997 | Cronin et al. | |
| 5,612,489 A | 3/1997 | Ragsdale et al. | |
| 5,679,576 A | 10/1997 | Kawai et al. | |
| 5,693,545 A | 12/1997 | Chung et al. | |
| 5,752,410 A * | 5/1998 | Bernstein | 73/514.18 |
| 5,827,947 A | 10/1998 | Miller et al. | |
| 5,827,952 A * | 10/1998 | Mansure et al. | 73/61.45 |
| 5,900,128 A | 5/1999 | Gumbrecht et al. | |
| 5,907,765 A | 5/1999 | Lescouzeres et al. | |
| 6,093,308 A | 7/2000 | Lewis et al. | |
| 6,100,587 A | 8/2000 | Merchant et al. | |
| 6,171,378 B1 | 1/2001 | Manginell et al. | |
| 6,179,413 B1 | 1/2001 | Coulman et al. | |
| 6,196,052 B1 | 3/2001 | May et al. | |
| 6,202,473 B1 | 3/2001 | Stokes et al. | |
| 6,236,046 B1 | 5/2001 | Watabe et al. | |
| 6,265,222 B1 * | 7/2001 | DiMeo et al. | 436/144 |
| 6,274,198 B1 | 8/2001 | Dautartas | |
| 6,284,666 B1 | 9/2001 | Naeem et al. | |
| 6,383,401 B1 | 5/2002 | Labzentis et al. | |
| 6,428,713 B1 | 8/2002 | Christenson et al. | |
| 6,443,179 B1 | 9/2002 | Benavides et al. | |
| 6,499,354 B1 * | 12/2002 | Najafi et al. | 73/723 |
| 6,553,354 B1 * | 4/2003 | Hausner et al. | 706/1 |
| 6,596,236 B2 | 7/2003 | Dimeo, Jr. et al. | |
| 6,618,174 B2 | 9/2003 | Parker et al. | |
| 6,634,213 B1 | 10/2003 | O'Connor et al. | |
| 6,694,800 B2 | 2/2004 | Weckstrom et al. | |
| 6,883,371 B2 | 4/2005 | Sugaya et al. | |
| 6,895,805 B2 | 5/2005 | Hoagland | |
| 7,080,545 B2 | 7/2006 | Dimeo, Jr. et al. | |
| 2001/0009652 A1 | 7/2001 | Arno | |
| 2002/0029613 A1 | 3/2002 | Stetter et al. | |
| 2002/0051132 A1 | 5/2002 | Ohno et al. | |
| 2004/0163444 A1 | 8/2004 | Dimeo, Jr. et al. | |
| 2004/0163445 A1 | 8/2004 | Dimeo, Jr. et al. | |
| 2005/0103097 A1 * | 5/2005 | Faltum et al. | 73/61.41 |
| 2005/0193800 A1 | 9/2005 | DeBoer et al. | |
| 2005/0230258 A1 | 10/2005 | Dimeo, Jr. et al. | |

FOREIGN PATENT DOCUMENTS

SU            1379632A A1     3/1988

OTHER PUBLICATIONS

Anderson, B, et al., Semiconductor International, Oct. 1993.
Inorganic Solid Fluorides, Chemistry and Physics, Academic Press, 1985, Ed P. Hagenmuller. (See Information Disclosure Statement Box 1).
W. Moritz, et al., Sensors and Actuators B 24-25 (1996) 194-196, "Monitoring of HF and F2 using a field-effect sensor".
Dr. Shigeru Kurosawa, et al., Fluorine in Coatings II, Paper 33, pp. 1-8, "Polymerisation of Fluorine Contained Polycyclic Compounds: Its Application in Chemical Sensors".
Werner Moritz, et al., The 11th European Conference on Solid State Transucers, Warsaw, Poland, pp. 111-114, Sep. 21-24, 1997, "Gas Sensors for Fluorine Using Different Semiconductor Substrates".
W. Moritz, et al., 1998 American Chemical Society, Chapter 10, pp. 119-129, "Silicon-Based Sensor for Fluorine Gas".
Semiconductor International, "Residual Gas Analysis", Oct. 1997, pp. 94-100.
Van Zant, Peter, Chapter 8: The ten-step patterning process—Surface preparation to exposure, Microchip Fabrication: A Practical Guide to Semiconductor Processing, 5th Ed., 2004, pp. 197-203, Publisher: McGraw-Hill, Published in: New York, NY.

* cited by examiner

NICKEL-COATED FREE-STANDING
SILICON CARBIDE STRUCTURE FOR
SENSING FLUORO OR HALOGEN SPECIES
IN SEMICONDUCTOR PROCESSING
SYSTEMS, AND PROCESSES OF MAKING
AND USING SAME

CROSS-REFERENCE TO RELATED
APPLICATIONS

This is a continuation-in-part of U.S. patent application Ser. No. 10/273,036 filed Oct. 17, 2002 for "APPARATUS AND PROCESS FOR SENSING FLUORO SPECIES IN SEMICONDUCTOR PROCESSING SYSTEMS" in the names of Frank Dimeo Jr., Philip S. H. Chen, Jeffrey W. Neuner, James Welch, Michele Stawasz, Thomas H. Baum, Mackenzie E. King, Ing-Shin Chen, and Jeffrey F. Roeder.

GOVERNMENT RIGHTS IN INVENTION

Work related to the invention hereof was conducted in the performance of NIST ATP Program, Contract Number 70NANB9H3018 for "Integrated MEMS Reactor Gas Monitor Using Novel Thin Film Chemistry for the Closed Loop Process Control and Optimization of Plasma Etch and Clean Reactions in the Manufacturing of Microelectronics." The Government has certain rights in the invention.

BACKGROUND OF THE INVENTION

1. Field of the Invention

The present invention relates generally to a device and a method for sensing fluoro or halogen species, which have utility for monitoring of fluorine-containing compounds and ionic species in semiconductor process operations.

2. Description of the Related Art

In the manufacture of semiconductor devices, the deposition of silicon (Si) and silicon dioxide ($SiO_2$), and subsequent etching, are vital operational steps that currently comprise 8-10 steps or roughly 25% of the total manufacturing process. Each deposition tool and etch tool must undergo a periodic cleaning procedure, sometimes as often as every run, in order to ensure uniform and consistent film properties.

Currently, in etching operations, etch endpoints are reached when a prescribed amount of time has elapsed. Over etch, in which the etch gas continues to flow into the reactor chamber after the cleaning etch is finished, is common and leads to longer process cycles, reduced tool lifetimes, and unnecessary global-warming-gas losses to the atmosphere (Anderson, B.; Behnke, J.; Berman, M.; Kobeissi, H.; Huling, B.; Langan, J.; Lynn, S-Y., *Semiconductor International*, October (1993)).

Similar issues are present in the etching of silicon nitride, tantalum oxide ($Ta_2O_5$), or silicon-based low dielectric constant materials (e.g., C- and/or F-doped $SiO_2$).

Various analytical techniques, such as FTIR, Optical Emission Spectroscopy, and Ionized Mass Spectroscopy, can be used to monitor the etch process. However, these techniques tend to be expensive, and often require a dedicated operator due to their complexity.

It would therefore be a significant advance in the art to provide a reliable, low-cost gas sensing capability that will serve to improve the throughput and chemical efficiency of the equipment used for the deposition and etching of silicon-containing materials, including silicon, silicon nitride and silicon dioxide, by reducing and optimizing clean and etch times, and hence reducing chemical usage, lengthening equipment operating life, and decreasing equipment down time.

U.S. patent application Ser. No. 10/273,036 filed Oct. 17, 2002 for "APPARATUS AND PROCESS FOR SENSING FLUORO SPECIES IN SEMICONDUCTOR PROCESSING SYSTEMS" discloses an apparatus and method for sensing solid-state fluoro or halogen species, using a fluoro- or halogen-reactive metal filament woven around metal packaging posts or Vespel® polyimide blocks on a KF flange. Detection of the fluoro species using such metal filament-based sensors relies on monitoring the resistance changes in the metal filaments caused by their reactions with the fluorine-containing compounds. In order to ensure acceptable sensitivity and signal-to-noise ratio for such metal filament-based sensors, the dimensions and the positions of the metal filaments are controlled and optimized via uses of the metal packaging posts or the Vespel® polyimide blocks, and the absolute resistance of such metal filaments are therefore adequate for endpoint detection.

However, the Vespel® structures and/or the metal packaging posts, when used in conjunction with the metal filament sensors, may form a heat sink that reduces the signal strength of the sensor elements. Further, fabrication of the 3-dimensional sensor packages containing the metal filaments, the metal posts and/or Vespel® blocks on the KF flange is relatively labor intensive.

It would therefore be a significant advance in the art to provide a micromachined sensing device that contains a free-standing resistance sensor element that is characterized by relatively high electrical resistance, high signal strength, and low heat loss.

It will be another object of the present invention to provide a micromachined sensing device that is suitable for automated and scale-up production.

Other objects and advantages will be more fully apparent from the ensuing disclosure and appended claims.

SUMMARY OF THE INVENTION

The present invention relates generally to apparatus and method for sensing fluoro species in an environment susceptible to the presence of such species, such as an ambient environment, a gaseous effluent stream from a semiconductor manufacturing process, etc.

In one aspect, the invention relates to a gas sensor assembly comprising a free-standing gas sensing element fabricated on a substrate, such gas sensing element comprising a sensor material exhibiting a detectable change upon contact with a target gas species or upon exposure to concentration fluctuations of the target gas species, means for detecting such change in the gas sensing element, and means for responsively generating an output signal.

Another aspect of the invention relates to a gas sensor assembly arranged to monitor a effluent from a semiconductor manufacturing plant or a fluid derived from the effluent, wherein the effluent or fluid derived therefrom is susceptible of comprising a target gas species, and the gas sensor assembly comprises a free-standing gas sensing element comprising a sensor material exhibiting a change in at least one property thereof upon contact with the target gas species in the effluent or a fluid derived from the effluent, such free-standing gas sensing element being coupled to means for monitoring the change in property and responsively generating an output signal.

The sensor material may comprise any suitable material that generates a measurable response to a target gas species.

Preferably, such sensor material comprises suitable metal or metal alloy that demonstrate a detectable change in at least one property thereof upon contact with fluorine-containing compounds, including but not limited to, $NF_3$, $SiF_4$, $C_2F_6$, HF, and activated species thereof, which are typically employed in semiconductor chamber cleaning. Many of the transition metals and noble metals (including, for example, but not limited to, Ni, Cu, Ti, V, Cr, Mn, Nb, Mo, Ru, Pd, Ag, Ir, Al, and Pt), which readily form various non-volatile fluorinated compounds in contact with fluorine-containing gaseous components and exhibit detectable changes in the electrical resistance thereof, are useful for the practice of the present invention. Nickel or nickel alloy is particularly preferred as a fluoro or halogen sensor material, due to its high electrical resistivity, small heat capacity, small density, and high temperature coefficient of resistivity, which maximizes the ratio of signal strength/response time upon contact with fluoro or halogen species.

The sensor material of the present invention may be provided in a free-standing form, i.e., which is structurally unsupported over a portion, preferably at least a major portion of its physical extent.

Alternatively, such sensor material is supported by a free-standing support structure that is characterized by high electrical resistance, low thermal mass, and high resistivity to corrosive fluorine-containing compounds. Such support structure may be fabricated by using silicon carbide, which demonstrates superior electronic, mechanical, and chemical properties, including but not limited to, high corrosion-resistance in harsh environments, and manufacturability in thin-film form suitable for forming microelectromechanical (MEMS) structures via microfabrication techniques. Such support structure may also be fabricated using etch resistant polymers.

In a preferred embodiment of the invention, the gas sensor assembly comprises a free-standing silicon carbide support structure having a layer of nickel or nickel alloy coated thereon, wherein the nickel or nickel alloy coating layer is reactive with fluorine-containing compounds and produces a detectable change in its electrical resistance upon contact therewith, and wherein the silicon carbide support structure that is characterized by low thermal mass, high electrical resistivity, and high fluorine resistivity.

A still further aspect of the invention relates to a method of monitoring a fluid locus for the presence of a target gas species therein, said method comprising:

exposing fluid at said fluid locus to a free-standing gas sensing element comprising a sensor material and exhibiting a change in at least one property thereof upon contact with the target gas species;

monitoring said at least one property of the gas sensing element during step (a); and responsively generating an output signal when the gas sensing element exhibits said change in at least one property of the gas sensing element, indicative of the presence of the target gas species in the fluid locus or a change in concentration of the target gas species in the fluid locus.

In another aspect, the invention relates to a method of manufacturing a gas sensor assembly, comprising the steps of:

providing a substrate member;

depositing a layer of a first molding material on the substrate member;

depositing a layer of a second molding material on the layer of the first molding material;

patterning such layer of the second molding material to provide recesses that defines a predetermined supporting structure;

depositing a layer of support material in the recesses over such layer of the first molding material;

selectively removing the layer of the second molding material, to form a protruding support structure over the layer of the first molding material;

depositing on the protruding support structure a layer of a sensor material; and selectively removing the layer of the first molding material to release the protruding support structure, thereby forming a free-standing gas sensing element comprising the released support structure with a layer of the sensor material coated thereover.

The present invention advantageously employs micromolding techniques to create planarized structural layers with smooth vertical sidewalls and featureless field areas. Sacrificial molding materials that can be subsequently removed by liquid- or gas-phase etching or other removal process are deposited and patterned to form a mold with recesses for defining a predetermined structure, into which a structural or support material is filled, followed by removal of the sacrificial molding materials to release the predetermined structure formed of the structural material. Suitable sacrificial molding materials for the practice of the present invention include, but are not limited to, polymers that are removable by ashing in the presence of $O_2$, or materials such as $SiO_2$ that are removable by a fluorine-containing plasma etch, or by appropriate chemical solution or solvent dissolution media.

Specifically, the first and the second molding materials as mentioned hereinabove may be the same or different. Preferably, the first and the second molding materials are characterized by different removability and are therefore removable at different conditions. More preferably, the structural or support material comprises silicon carbide that is resistant to fluorine-containing plasma, while the first molding material comprises silicon dioxide that is removable by fluorine-containing plasma, and the second molding material comprises polysilicon readily removable by various chemical etchants, such as potassium hydroxide (KOH), ethylenediamine and pyrocatechol (EDP), which have no significant effect on silicon dioxide.

Therefore, in a most preferred embodiment of the present invention, the support material comprises silicon carbide; the first molding material comprises silicon oxide; the second molding material comprises polysilicon; and the sensor material comprises nickel or nickel alloy.

Yet another aspect of the invention relates to a gas sensor assembly including a free-standing metal sensor element arranged for selective resistance heating of the element and exhibiting a change in at least one property of the element in contact with a fluoro or halogen species in a gaseous environment, and a signal generator operatively coupled with the sensing element to output a signal indicative of presence of a fluoro or halogen species in gas being monitored when the gas being monitored is contacted with the sensing element and the gas being monitored contains such fluoro or halogen species.

A still further aspect of the invention relates to a free-standing gas sensing element comprising a released support structure coated with a layer of a sensor material responsive to presence of fluoro or halogen species or fluctuation in concentration of such fluoro or halogen species. Preferably, the released support structure comprises silicon carbide, while the sensor material comprises nickel or nickel alloy.

In another aspect, the invention relates to a gas sensor assembly comprising a micro-hotplate structure including a free-standing gas sensing element as described hereinabove, for precise temperature control of the free-standing gas sensing element.

Another aspect of the invention relates to a gas sensor assembly comprising a free-standing gas sensing element arranged for contact with a gaseous environment susceptible to the presence or change of concentration of one or more target gas species therein, wherein said free-standing gas sensing element comprises a released support structure coated with a layer of a sensor material, which in exposure to the target gas species exhibits a response indicative of the presence or change of concentration of the target gas species in said gaseous environment, wherein said gas sensor assembly further comprises spaced-apart upstanding contacts for supporting the free-standing gas sensing element.

In a still further aspect, the invention relates to a gas sensor assembly formed on a substrate member and arranged for contact with a gaseous environment susceptible to the presence or change of concentration of one or more target gas species therein, said gas sensor assembly comprising a free-standing gas sensing element comprising a released support structure coated with a layer of a sensor material, which in exposure to the target gas species exhibits a response indicative of the presence or change of concentration of the target gas species in said gaseous environment, wherein said gas sensor assembly further comprises a barrier layer comprising a material resistant to the target gas species, for protecting the substrate member thereunder.

In a still further aspect, the invention relates to a gas sensor assembly formed on a substrate member and arranged for contact with a gaseous environment susceptible to the presence or change of concentration of one or more target gas species therein, said gas sensor assembly comprising a free-standing gas sensing element comprising a released support structure coated with a layer of a sensor material, which in exposure to the target gas species exhibits a response indicative of the presence or change of concentration of the target gas species in said gaseous environment, wherein said gas sensor assembly further comprises a contact/barrier element having spaced-apart upstanding contacts formed over a barrier layer, said spaced-apart upstanding contacts supporting the free-standing gas sensing element, and said barrier layer comprising a material resistant to the target gas species for protecting the substrate member thereunder.

In yet another aspect, the invention relates to a method of manufacturing a gas sensor assembly arranged for contact with a gaseous environment susceptible to the presence or change of concentration of one or more target gas species therein, said method comprising the steps of:

providing a substrate member;

depositing a layer of a first molding material on the substrate member;

patterning said layer of the first molding material to form at least one barrier recess that defines a predetermined barrier structure;

depositing a layer of a barrier material resistant to the target gas species in such barrier recess and overlaying the substrate member;

depositing a layer of a second molding material on the layer of the first molding material and the layer of the barrier material;

patterning such layer of the second molding material to provide contact recesses defining one or more predetermined spaced-apart contacts on the layer of barrier material;

depositing a layer of a contact-forming material in such contact recesses and overlaying such layer of the barrier material;

depositing a layer of a third molding material on the layer of the second molding material and the layer of the contact-forming material;

patterning such layer of the third molding material to provide support recesses for defining a predetermined support structure overlaying both the layer of the contact-forming material and the layer of the second molding material;

depositing a layer of a support material in such support recesses and overlaying both the layer of the contact-forming material and the layer of the second molding material;

selectively removing the third molding material, to form a protruding support structure overlaying both the layer of the contact-forming material and the layer of the second molding material;

depositing a layer of a sensor material on the protruding support structure; and selectively removing the first and the second molding materials, thereby forming a free-standing gas sensing element comprising the released support structure coated with the sensor material, and a contact/barrier element comprising spaced-apart upstanding contacts formed over a barrier layer, wherein such free-standing gas sensing element is supported by such spaced-apart upstanding contacts of the contact/barrier element, and wherein the barrier layer of the contact/barrier element covers and protects the substrate member thereunder.

As used herein, the term "fluoro species" is intended to be broadly construed to encompass all fluorine-containing materials, including without limitation, gaseous fluorine compounds, fluorine per se in atomic and diatomic ($F_2$) forms, fluorine ions, and fluorine-containing ionic species. The fluoro species may for example include species such as $NF_3$, $SiF_4$, $C_2F_6$, HF, $F_2$, $COF_2$, $ClF_3$, $IF_3$, etc., and activated fluorine-containing species (denoted collectively as F*) thereof, including ionized fragments, plasma forms, etc.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
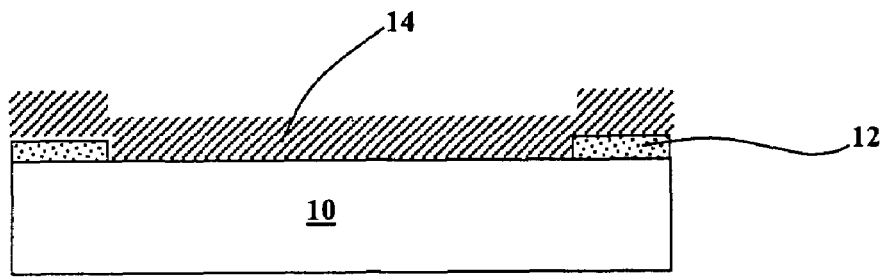
FIG. 1 illustratively depicts the cross-sectional view of a silicon substrate having a first sacrificial mold layer and a layer of barrier material deposited thereon.

The contents of U.S. patent application Ser. No. 10/273,036 filed Oct. 17, 2002 for "APPARATUS AND PROCESS FOR SENSING FLUORO SPECIES IN SEMICONDUCTOR PROCESSING SYSTEMS" and U.S. Pat. No. 6,265,222 issued Jul. 24, 2001 for "MICRO-MACHINED THIN FILM HYDROGEN GAS SENSOR, AND METHOD OF MAKING AND USING THE SAME" are incorporated herein by reference in their entirety for all purposes.

While the invention is described more fully hereinafter with specific reference to applications in semiconductor process control, it is to be appreciated that the utility of the invention is not thus limited, but rather extends to a wide variety of other uses and applications, including, without limitation, deployment in life safety systems, room or ambient environment monitoring operations, and other industrial as well as consumer market gas sensing applications.

The present invention in one aspect thereof provides microelectromechanical system (MEMS)-based gas sensing capability for determining the endpoints of semiconductor chamber clean processes.

Conventional MEMS designs (for other, more benign gas environments) require deposition of the sensing metal layers on a silicon-based device structure, and subsequent bonding and packaging of the device into a chip carrier. This current fabrication approach entails a multi-step process, involving a corresponding multicomponent product sensor assembly in which each component is subject to chemical attack by the heavily fluorinated gases. While it may be possible to protect each of the respective components by developing a suitable encapsulation structure, such expedient adds further fabrication complexity, manufacturing time and cost to the product gas sensor device.

The present invention overcomes these obstacles in a manner enabling the use of a MEMS-based sensor device that is easily and inexpensively fabricated, and readily implemented for monitoring fluorinated gases in semiconductor chamber clean processes in an efficient, durable and reliable manner in the harsh chemical environment of such processes.

The fluorinated gas sensor device of the present invention, as described more fully hereinafter, has multiple advantageous features that distinguish it as a breakthrough in the art. One such feature is the use in the device of high performance fluorine-reactive metal sensing elements, such as nickel or nickel alloy, which are characterized by high electrical resistance, low thermal mass, small density, and high temperature coefficient of resistivity that are particularly suitable for resistance-based gas sensing. The second feature relates to use of the metal elements both as a sensing material and as a heat source (e.g., by resistive, conductive, or other heating thereof) for the gas sensing operation, as for example where it is desired to vary the sensing temperature from ambient conditions, or to match the temperature of a semiconductor chamber whose effluent includes the target gas species to be monitored. The third such features relates to the use of silicon carbide (SiC) in conjunction with $SiO_2$/polysilicon sacrificial materials for forming free-standing silicon carbide support structure, which eliminates formation of heat sinks in connection with the metal sensing element and therefor minimizes the heat loss therefrom. The fourth feature relates to the use of micro-molding techniques for fabricating planarized structural layers, which allows automated and scale-up production of the gas sensing devices of the present invention and which provides high precision over product quality control. Such features as described hereinabove are independent of each other and can be incorporated either separately or jointly. The substrate and/or support material may alternatively be fabricated from an etch resistant polymeric material.

The fluoro or halogen species sensor device of the invention may include a single sensing element in any of the numerous suitable forms described hereinafter.

Alternatively, the fluoro or halogen species sensor device may comprise a plurality of such sensing elements, wherein the multiple elements provide redundancy or back-up sensing capability, or in which different ones of the multiple sensing elements are arranged for sensing of different fluoro or halogen species in the stream or gas volume being monitored, or in which different ones of the sensing elements in the array are operated in different modes, or in interrelated modes, such as for production of respective signals that are algorithmically manipulated, e.g., subtractively, to generate a net indicating signal, or alternatively, additively to produce a composite indicating signal, or in any other suitable manner in which the multiplicity of sensor elements is efficaciously employed to monitor the flow of species in the stream or fluid volume of interest, for generation of correlative signal(s) for monitoring or control purposes.

As is well known, fluorine reacts with most metals, and gives rise to compounds that have a high, and sometimes, mixed oxidation state (Inorganic Solid Fluorides, Chemistry and Physics. Academic Press, 1985, Ed P. Hagenmuller). Many of the transition metals and noble metals (including, for example, but not limited to, Ti, V, Cr, Mn, Nb, Mo, Ru, Pd, Ag, Ir, Ni, Al, Cu and Pt) readily form various nonvolatile fluorinated compounds in contact with fluorine gas components. The gas sensing device and method of the present invention use free-standing forms of these metals to detect the presence of fluorinated species in the gas being monitored.

The choice of a specific sensing material of construction may be readily determined for a given end-use application of the invention, by simple experiment involving exposure of candidate gas sensing element materials of construction to the fluoro or halogen species-containing environment, and determining the suitability, e.g., corrosion-resistance or etch-resistance, of the candidate materials in such exposure.

Nickel or nickel alloy (such as Monel) is particular preferred as a fluoro or halogen sensing material, due to its high fluorine-resistivity, high electrical resistance, low thermal mass, small density, and high temperature coefficient of resistivity. The ratio of signal strength/response time in resistance-based gas sensing operation is significantly influenced by the material properties of the sensor material, and nickel or nickel alloy-based sensor elements have been discovered to provide the maximum signal strength/response time ratio among metal sensor elements, when the sensor form/dimension and the instrumentational factors provided are the same.

Detection of the fluoro or halogen species of interest may be achieved in any suitable manner, e.g., by means of a change in resistance of the free-standing metal material as it reacts with fluorine-containing species.

The metal sensing element in fluorine detectors of the invention may be provided in any of numerous suitable forms, and may have tailored morphology, such as roughened surfaces or induced nanoporosity. The resistance and behavior of the metal element can be engineered by altering the geometry of the structure. For example, the geometry of a suspended metal thin film can be engineered by choosing the width, length and thickness of the film over the suspended area appropriately. A suspended metal filament can be thinned after fabrication thereof, in any of a variety of ways, e.g., mechanically, chemically, electrochemically, optically or thermally, in order to increase the absolute resistance, as well as to increase the surface area-to-volume ratio of the metal, to thereby increase the sensitivity or improve the signal-to-noise ratio. Further, the material's physical properties can be engineered. For example, the composition can be modified either by alloying or doping, and the microstructure can be modified, e.g., by change in grain size, level of crystallinity, porosity (e.g., nanoporosity), surface area-to-volume ratio, etc.

It will therefore be apparent that the metal sensing element may be variously configured and modified as desired with respect to its form, conformation, physical properties, chemical properties and morphological character, within the skill of the art and without undue experimentation.

The reaction of the fluorine compound with the metal sensing element may be temperature-sensitive, and heating of the metal can be achieved by passing current through it. In this way, the metal sensing elements may be utilized in the gas sensing operation concurrently as heating structures.

In order to enhance the sensitivity and signal-to-noise ratio of the gas sensor of the invention, a fluoro- or halogen-sensitive metal thin film is deposited on a free-standing silicon carbide support structure that is characterized by high electrical resistance and low thermal mass. The high electrical resistance of such SiC support structure further enhances the sensitivity and signal strength of the sensor; the low thermal mass of SiC minimizes potential heat loss from the support structure; and such SiC support structure, being free-standing itself, effectively isolates the metal sensing film from the substrate and enhance the signal-to-noise ratio.

Such free-standing silicon carbide support structure may be fabricated by: (1) providing on a substrate a sacrificial mold having recesses therein that define a predetermined support structure, (2) depositing a SiC film into the recesses of such sacrificial mold, and (3) selectively removing the sacrificial mold, to form a free-standing SiC support structure that is separated from the substrate by air gaps or empty spaces originally occupied by such sacrificial mold.

The sacrificial mold may be formed by depositing a layer of sacrificial materials and then patterning such layer to form the necessary recesses that define the predetermined support structure. Any suitable materials that are selectively removable in connection with the support structure may be used as the sacrificial materials for the practice of the present invention. For example, silicon dioxide is selectively removable by fluorine-containing compounds such as HF, in connection with the silicon carbide support structure that is resistant to the fluorine-containing compounds.

After formation of the support structure, a layer of a fluoro- or halogen-sensing material, preferably a fluoro- or halogen-reactive metal or metal alloy, may be coated over such support structure, to form a free-standing gas sensing assembly that is responsive to the presence of fluoro or halogen species.

One or more spaced-apart upstanding contacts may be provided to support such free-standing gas sensing assembly, preferably only at its peripherals. More preferably, such spaced-apart upstanding contacts comprise materials of high electrical resistance, low thermal mass, and high resistance to corrosive fluorine-containing compounds. Silicon carbide is particularly preferred for forming such contacts.

When the free-standing gas sensing assembly is formed over a substrate (such as silicon substrate) that is susceptible to attacks by the corrosive fluorine-containing compounds, a barrier layer that is resistant to such compounds is preferably provided to cover and protect the substrate. Such barrier layer may comprise any fluoro or halogen resistant materials, including but not limited to polyimide and silicon carbide, among which silicon carbide is preferred.

One preferred embodiment of the present invention relates to a gas sensor assembly that comprises a free-standing gas sensing element, one or more spaced-apart upstanding contacts, and a barrier layer, while the spaced-apart contacts are fabricated on the barrier layer, forming an integral contact/barrier element for supporting the free-standing gas sensing element and for covering and protecting the substrate member thereunder.

Referring now to the drawings FIGS. 1-10A, which are schematic illustrations depicting the process flow in the manufacture of a gas sensing assembly that comprises a free-standing gas sensing element and a contact/barrier element as described hereinabove, according to one embodiment of the present invention.

As shown in FIG. 1, a substrate member 10 is provided, upon which a layer of a first sacrificial molding material (preferably silicon dioxide) 12 is deposited and patterned, to form a barrier recess therein. A layer of a barrier material (preferably silicon carbide) 14 is deposited in such barrier recess on substrate member 10 as well as on the first sacrificial molding material 12, and then planarized to expose the first sacrificial molding material 12, as shown in FIG. 2.

The planarization step improves the planarity of the structural layers, and assists thereby in achieving good control of the geometry of the subsequently formed structural layers. The planarization step is optional, and may be omitted in instances where good self-leveling behavior is demonstrated by the barrier material, and it is possible to apply the barrier material into the barrier recesses so as to be near-level with the adjacent surface of the first sacrificial molding material surrounding such recesses.

Figure 2:
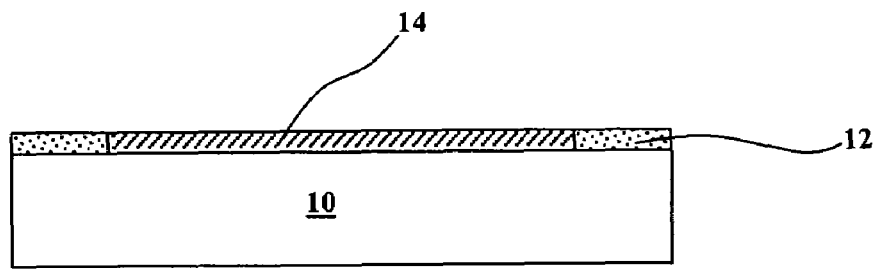
FIG. 2 illustratively depicts the cross-sectional view of the structures of FIG. 1, except that the layer of barrier material is planarized to be coplanar with the first sacrificial mold layer.
Figure 2A:
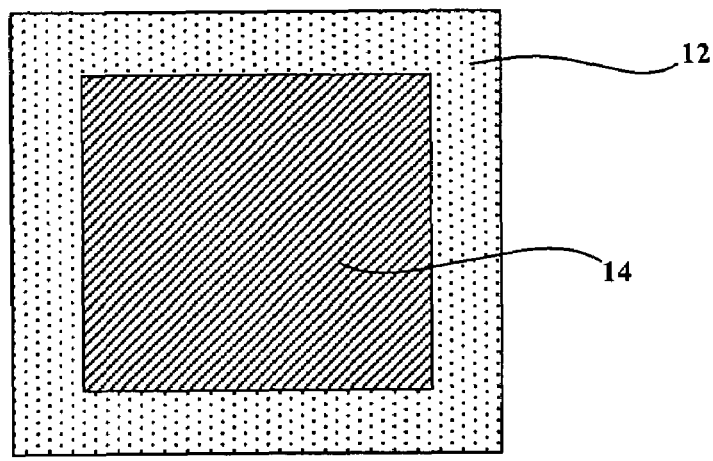
FIG. 2A shows the top view of the structures of FIG. 2.

FIG. 2A shows the illustrative top view of the structures of FIG. 2, from which the first sacrificial molding material 12 is visible, with a square-shaped barrier recess filled with the barrier material 14 therein. Please note that the shape and conformation of the barrier recess can be readily modified by a person ordinarily skilled in the art, according to the specific end use and system requirements, and are therefore not limited by the illustrative example provided herein.

Figure 3:
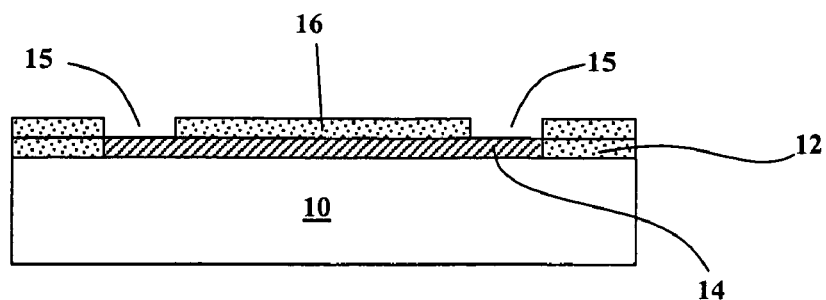
FIG. 3 illustratively depicts the cross-section view of the structures of FIG. 2, further having a second sacrificial mold layer formed thereon.

A layer of a second sacrificial molding material (preferably silicon dioxide) 16 is further deposited on the planarized barrier material 14 and the first sacrificial molding material 12, and patterned to provide contact recesses 15, which defines one or more spaced-apart contacts that are positioned over the planarized barrier material 14, as shown in FIG. 3.

Figure 4:
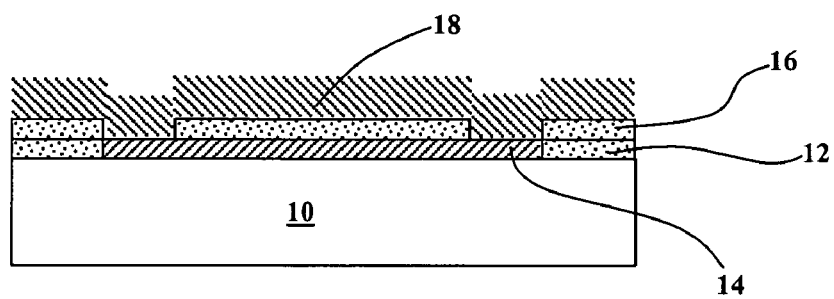
FIG. 4 illustratively depicts the cross-sectional view of the structures of FIG. 3, further having a layer of contact-forming material deposited thereon.
Figure 5:
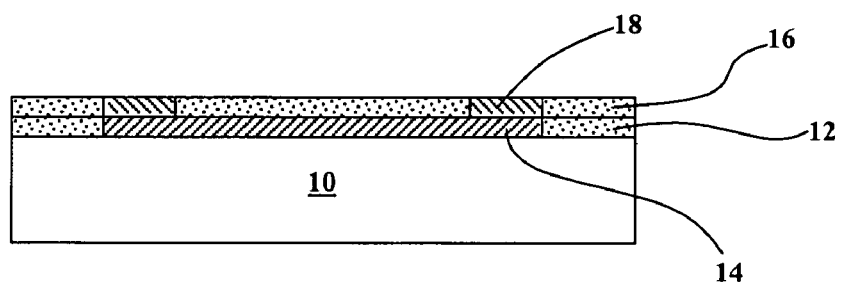
FIG. 5 illustratively depicts the cross-sectional view of the structures of FIG. 4, except that the layer of contact-forming material is planarized to be coplanar with the second sacrificial mold layer.
Figure 5A:
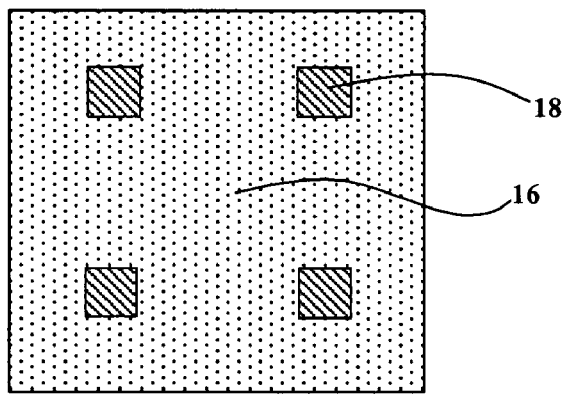
FIG. 5A shows the top view of the structures of FIG. 5.

A contact-forming material (preferably silicon carbide) 18 is then deposited into such contact recesses and planarized to expose the second sacrificial molding material 16, as shown in FIGS. 4-5. FIG. 5A provides the top view of the structures of FIG. 5, from which the second sacrificial molding material 16 is visible. Four spaced-apart square contact recesses are formed in the second sacrificial molding material 16 and are filed with the contact-forming material 18.

Figure 6:
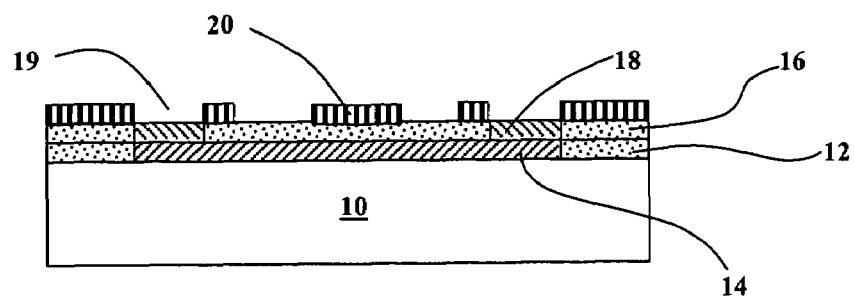
FIG. 6 illustratively depicts the cross-sectional view of the structures of FIG. 5, further having a third sacrificial mold layer formed thereon.

FIG. 6 shows deposition and patterning of a layer of a third sacrificial molding material (preferably polysilicon) 20, which contains structural recesses 19 that define a predetermined support structure. Specifically, such structural recesses 19 are positioned above both the contact-forming material 18 and the second sacrificial molding material 16, and the support structure so defined therefore bridges over the spaced-apart contacts and the second sacrificial molding material 16.

Figure 7:
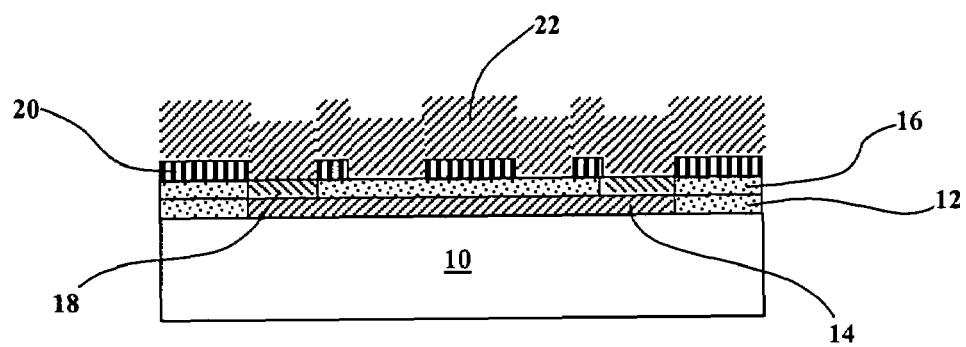
FIG. 7 illustratively depicts the cross-sectional view of the structures of FIG. 6, further having a layer of support material deposited thereon.
Figure 8:
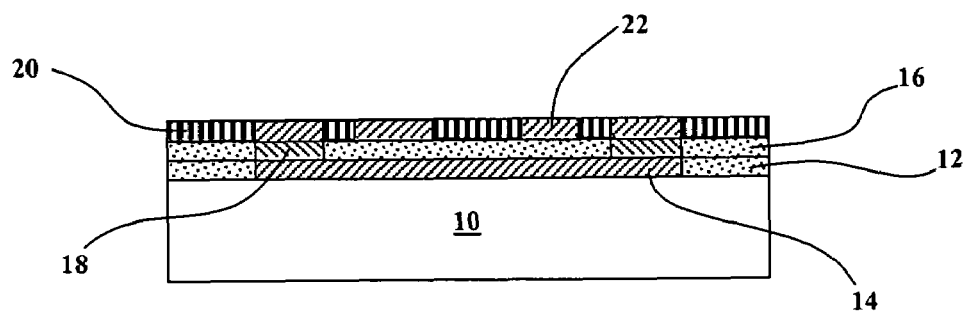
FIG. 8 illustratively depicts the cross-sectional view of the structures of FIG. 7, except that the layer of support material is planarized to be coplanar with the third sacrificial mold layer.

FIGS. 7-8 shows deposition of a layer of a support material (preferably silicon carbide) 22 in such structural recesses, and subsequent planarization thereof to expose third sacrificial molding material 20.

Figure 8A:
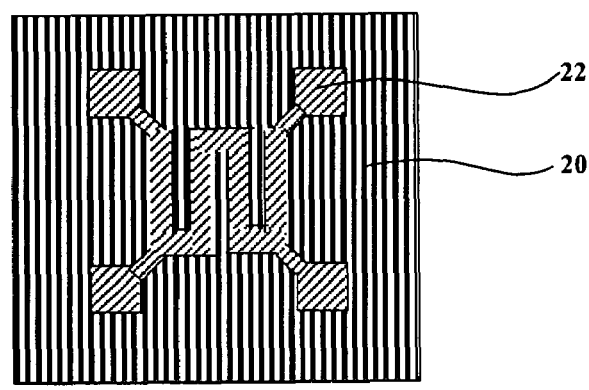
FIG. 8A shows the top view of the structures of FIG. 8.

FIG. 8A shows the top view of the structures in FIG. 8, comprising a support structure 22 formed in the structure recesses in the third sacrificial molding material 20, while such support structure 22 bridges over the four spaced-apart contacts (not visible in FIG. 8A) and the second sacrificial molding material 16 (not visible in FIG. 8A).

Figure 9:
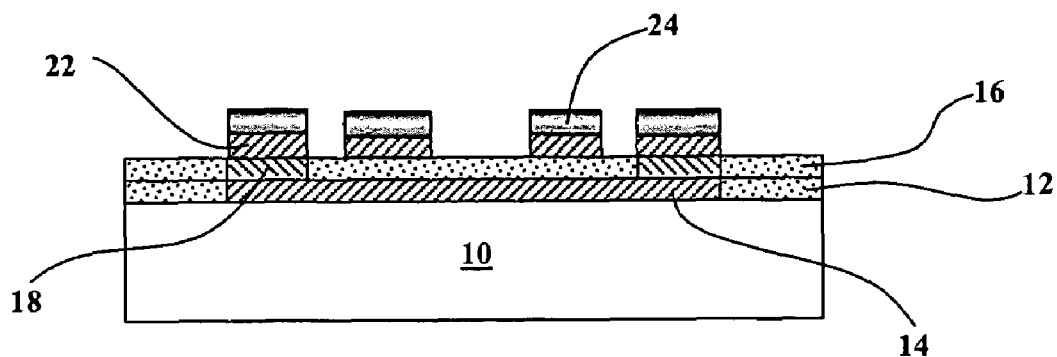
FIG. 9 illustratively depicts the cross-sectional view of the structures of FIG. 8, except that the third sacrificial mold layer is selectively removed and a layer of a sensor material is deposited thereon.
Figure 9A:
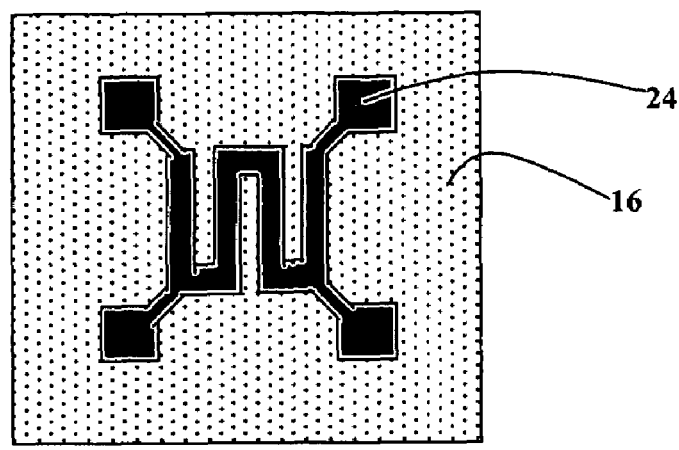
FIG. 9A shows the top view of the structures of FIG. 9.

In FIG. 9, the third sacrificial molding material 20 is selective removed, thereby forming a protruding support structure formed of the support material 22 and exposing the second sacrificial molding material 16, and a layer of a fluorine-reactive metal or metal alloy (preferably containing nickel) 24 is deposited over such protruding support structure. FIG. 9A shows the top view of the structures of FIG. 9, from which the second sacrificial molding material 16 and the fluorine-reactive metal or metal alloy 24 are visible.

Finally, the first and the second sacrificial molding materials 12 and 16 are selectively removed, forming a free-standing gas sensing element comprising the support structure 22 and the fluorine-reactive metal layer 24 thereon, and a contact/barrier element comprising the spaced-apart contacts 18 and the barrier layer 14. The free-standing gas sensing element is supported by spaced-apart contacts 18 at its peripheral, while the central major portion of such gas sensing element is suspended and isolated. The barrier layer 14 supports the contacts 18 thereon and protects the underlying substrate member 10 from potential attacks by corrosive fluorine-containing compounds.

Figure 10:
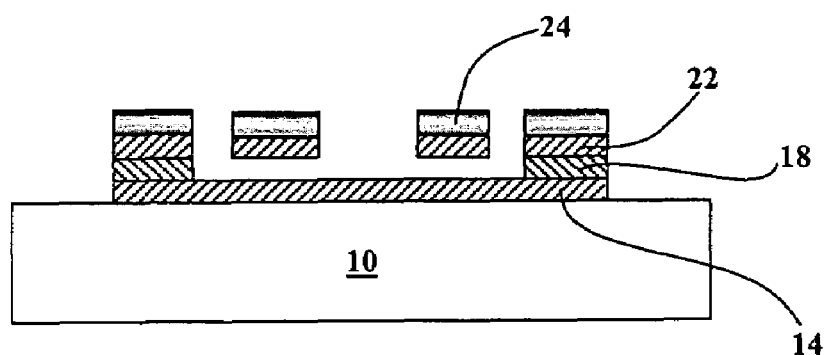
FIG. 10 illustratively depicts the cross-sectional view of the structures of FIG. 9, except that the first and the second sacrificial molding layers are selectively removed, forming a free-standing gas sensing element and a contact/barrier element according to one embodiment of the present invention.
Figure 10A:
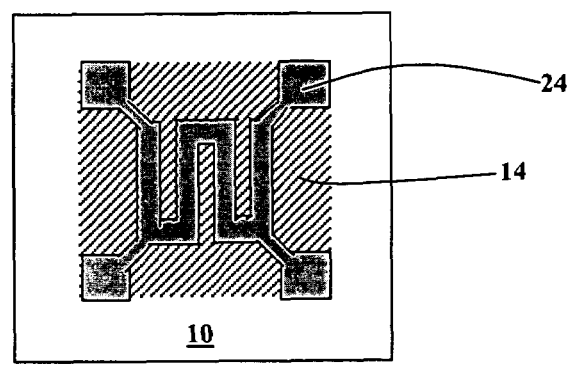
FIG. 10A shows the top view of the structures of FIG. 10.

FIG. 10A shows the top view of the structures of FIG. 10, in which only the metal layer 24 of the free-standing gas sensing element and the barrier layer 14 of the contact/barrier element are visible.

Figure 11:
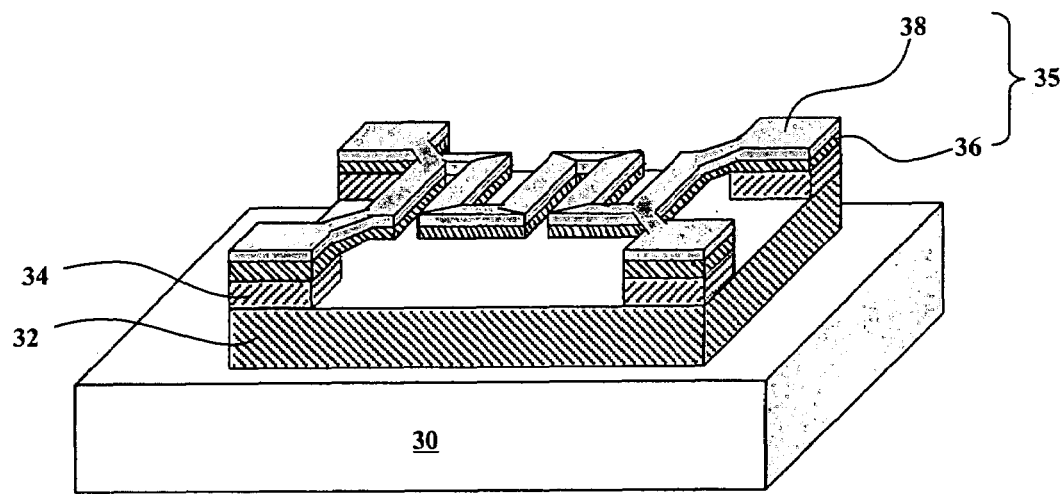
FIG. 11 is a perspective view of an illustrative gas sensor assembly, comprising a free-standing gas sensing element supported by a contact/barrier element, according to one embodiment of the present invention.

FIG. 11 is a perspective view of a gas sensor assembly according to one embodiment of the present invention, which comprises a free-standing gas-sensing element 35 containing a silicon carbide layer 36 having a nickel coating 38 thereon. Such gas-sensing element 35 is supported at its peripheral by spaced-apart upstanding contacts 34. A barrier layer 32 provides support to the spaced-apart contacts 34 as well as protects the underlying substrate 30 from the harsh chemical conditions imposed by the corrosive target gas species during the gas sensing operations.

The gas-sensing element 35 suspends over the barrier layer 32 as well as the substrate 30 thereunder, and only peripherally contacts the spaced-apart contacts 34 at very limited areas. Therefore, the majority surface area (preferably more than 80% surface area, and more preferably more than 95%) of the gas-sensing element 35 is suspended and isolated from the substrate 30 by air cavity. Further, by forming the spaced-apart contacts 34 with materials characterized by high electrical resistance and low thermal mass (e.g., silicon carbide), potential heat loss from the gas-sensing element 35 can be minimized. Further, the gas assembly of the present invention is formed of fluorine-resistant materials such as silicon carbide, and therefore is particularly robust and reliable in gaseous environment susceptible to presence of fluorine-containing compounds.

The free-standing gas sensing element in the gas sensor assembly of the invention is preferably of a high surface to volume (S/V) character, to facilitate rapid response, and to amplify the response relative to the substantially lower change in the gas-indicating bulk property that would otherwise occur in a low S/V conformation of the same sensor material.

Thus, the critical dimension of the free-standing gas sensing element—the thickness dimension for foils or films, or the diameter for forms such as filaments, bars, or columns, etc.—desirably is less than 500 microns ($\mu m$), preferably less than 150 $\mu m$, more preferably less than 25 $\mu m$, still more preferably is less than 10 $\mu m$, and most preferably is in a range of from about 0.1 $\mu m$ to about 5 $\mu m$, as a balance of response speed and ease of fabrication considerations.

Foils and films, in addition to having a low thickness, e.g., in a range of from about 0.1 $\mu m$ to about 50 $\mu m$, desirably have small dimensional characteristics in the plane perpendicular to the thickness direction of the foil or film, again for reasons of responsivity. The lateral dimensions in such plane (x-y plane, where the z axis is the thickness direction) include a length x-direction) and width (y-direction) that are advantageously less than about 10 cm, preferably being less than about 1 mm and more preferably less than about 100 $\mu m$, e.g., in a range of from about 20 $\mu m$ to about 5 mm, as a balance of fabricational complexity and responsiveness. In general, suitable dimensions of sensor wires can be readily determined to provide correspondingly suitable signal-to-noise ratios for the intended applications.

In the context of the foregoing description, it is to be appreciated that the free-standing gas sensing element could be fabricated as a nano-scale element, albeit as a more costly gas sensor product than the typically millimeter/micrometer-scale elements discussed above.

In instances where multiple metal sensing element structures are provided, different ones of the multiple metal structures may be constructed and arranged for sensing of different fluorinated species in the fluid environment being monitored, and/or same fluorinated species at different temperatures, and different geometries and configurations of sensing elements may be employed for redundancy and/or ensuring accuracy, etc. Alternatively, or additionally, different ones of the multiple sensing elements may be operated in different operating modes, e.g., resistively, conductively, pulsed, a DC mode, an AC mode, etc.

In connection with the use of arrays of gas sensing elements, advanced data processing techniques can be used to enhance the output of the sensor system. Examples of such techniques include, but are not limited to, the use of compensating signals, the use of time-varying signals, heater currents, lock-in amplifying techniques, signal averaging, signal time derivatives, and impedance spectroscopy techniques. In addition, advanced techniques that fall into the category of chemometrics may also be applied. These techniques include least squares fitting, inverse least squares, principal component regression, and partial least square data analysis methods.

For example, on being contacted by fluorine compound(s) such as $SiF_4$, and/or other fluoro or halogen species, the voltage across the metal sensing element (as a component of an electrical circuit) may drop, indicative of an increase in resistance of the metal sensing element incident to its contact with a target fluoro or halogen species. Such voltage drop can be employed to generate a signal for process control purposes. The voltage drop can be employed to generate a signal that actuates an automatic control valve, to effect flow initiation, flow termination, or flow switching of a process stream in the semiconductor process system. The control signal alternatively may be employed to actuate a cycle timer, to initiate a new step in the process operation, or to signal that a maintenance event, such as change-out of a scrubber resin in an abatement process chamber, is necessary or desirable.

It will be appreciated that the change in properties of the metal sensing element can be exploited in any of a variety of ways, to effect the control of a process in relation to the sensing of the target gas (e.g., fluoro or halogen) species, within the skill of the art and without undue experimentation.

By way of further examples, the sensor assembly of the invention may be utilized in connection with a gas cabinet containing a supply of a fluoro or halogen species gas (such as a perfluoro species, e.g., a perfluorinated organometallic precursor for chemical vapor deposition operations), and the gas sensor assembly may be employed to determine the existence of a leak from the supply vessel or otherwise in the flow circuitry in the gas cabinet. The sensing of the fluoro or halogen species then may be utilized to actuate a source of bulk purge gas, to sweep out the interior volume of the gas cabinet and prevent the concentration of the fluoro or halogen species from reaching toxic or otherwise hazardous levels.

The sensor assembly may also be utilized in a monitoring unit for an ambient environment that is susceptible to the ingress or generation of fluoro or halogen species therein, or alternatively the sensor assembly could be a constituent part of a wearable gas monitoring unit that is arranged to actuate an alarm and/or a self-contained source of emergency breathing gas, for hazardous materials cleanup crews, firefighters in chemical complexes, workers in HF glass-etching operations, etc.

The gas sensor assembly of the invention is readily applicable to monitoring of fluoro or halogen species in various industrial process operations generating such species, including semiconductor manufacturing operations such as chamber cleans, in which fluoro or halogen species are utilized for removing silicon oxides, silicon nitrides, tantalum oxides, and low dielectric constant (k<3.9) silicon-containing films such as carbon-doped silicon oxides, etc.

A variety of designs are possible for the gas sensing assembly of the present invention, and an array of devices of different dimensions may be advantageously employed to maximize the efficiency of the gas sensor assembly, in respect of generation and outputting of a plurality of signals for the monitoring of the one or more target gas species in the fluid environment being monitored by the assembly.

It will be recognized that micro-hotplate embodiments of the gas sensing assembly of the present invention may be widely varied in respect of the component sensing films and reactive/sorptive chemistries employed, as determinable within the skill of the art for a given end use application of target gas species detection. Micro-hotplate detectors of a type adaptable to the practice of the present invention may be fabricated as more fully described in U.S. Pat. No. 6,265,222 issued Jul. 24, 2001 in the names of Frank DiMeo, Jr. and Gautam Bahndari, the disclosure of which hereby is incorporated herein by reference in its entirety.

Although the invention has been variously described herein with reference to illustrative embodiments and features, it will be appreciated that the embodiments and features described hereinabove are not intended to limit the invention, and that other variations, modifications and other embodiments will readily suggest themselves to those of ordinary skill in the art, based on the disclosure herein. The invention therefore is to be broadly construed, consistent with the claims hereafter set forth.

What is claimed is:

1. A gas sensor assembly for sensing halogen species comprising:
   a substrate having a substrate surface; and
   at least one gas sensor, wherein the gas sensor comprises:
      a free-standing support structure, wherein the free standing support structure comprises at least two spaced apart contacts that project above the substrate surface into an air cavity and a lateral surface that spans between the projecting contacts with an air cavity therebeneath, wherein the free-standing support structure is fabricated of a support material that is resistant to the halogen species; and
      a metal gas sensor element positioned on at least the lateral surface of the free-standing support structure, wherein said metal sensor element comprises a metal or metal alloy exhibiting a detectable change upon contact with a halogen species.

2. The gas sensor assembly of claim 1, wherein the metal sensor element comprises a transition metal or a noble metal.

3. The gas sensor assembly of claim 1, wherein the metal sensor element comprises Ni or Ni alloy.

4. The gas sensor assembly of claim 1, wherein the free-standing support structure comprises silicon carbide.

5. The gas sensor assembly of claim 1, wherein the free-standing support structure comprises an etch-resistant polymer.

6. The gas sensor assembly of claim 1, further comprising means for monitoring the change in the metal sensor element upon contact thereof with the halogen species, and means for responsively generating an output signal.

7. The gas sensor assembly of claim 1, wherein contacting of the halogen species with the metal sensor element effects a temperature-sensitive reaction of the halogen species and the metal sensor element, and wherein the assembly is constructed and arranged for passing current through the metal sensor element, for heating thereof to facilitate the temperature-sensitive reaction.

8. The gas sensor assembly of claim 1, comprising a multiplicity of said metal sensor elements, forming an array.

9. The gas sensor assembly of claim 8, wherein the array is constructed and arranged to monitor different halogen species, and/or to operate in different operating modes in different elements of the array.

10. The gas sensor assembly of claim 8, wherein the array is constructed and arranged to monitor the same halogen species at different process conditions.

11. A gas sensor assembly comprising:
a substrate; and
a free-standing silicon carbide support structure comprising:
at least one protruding support rising above the substrate and a lateral structure contacting the protruding support, wherein the lateral surface is coated with a layer of nickel or nickel alloy, wherein said nickel or nickel alloy layer is adapted to exhibit a response indicative of the presence or change of concentration of a target gas species.

12. A gas sensor assembly comprising:
a substrate; and
a free-standing gas sensing element positioned on the substrate and arranged for contact with a gaseous environment susceptible to the presence or change of concentration of one or more target gas species therein, wherein said free-standing gas sensing element comprises:
a suspended support structure comprising at least one protrusion rising above the substrate and a lateral surface contacting the protrusion and extending beyond the protrusion to form an air gap thereunder and wherein at least the lateral surface is coated with a layer of a gas sensing material, and wherein said gas sensing material in exposure to the target gas species exhibits a response indicative of the presence or change of concentration of the target gas species in said gaseous environment.

13. The gas sensor assembly of claim 12, further comprising multiple spaced-apart contacts for supporting the free-standing gas sensing element.

14. The gas sensor assembly of claim 13, wherein said spaced-apart contacts comprise a material resistant to the target gas species.

15. The gas sensor assembly of claim 14, wherein the target gas species comprises halogen-containing compounds, and wherein the spaced-apart contacts comprises silicon carbide.

16. The gas sensor assembly of claim 14, wherein said barrier layer comprises a material resistant to the target gas species.

17. The gas sensor assembly of claim 16, wherein the target gas species comprises halogen-containing compounds, and wherein the barrier layer comprises silicon carbide or an etch-resistant polymer.

18. The gas sensor assembly of claim 13, wherein the free-standing gas sensing element is supported only by said spaced-apart contacts.

19. The gas sensor assembly of claim 12, further comprising a barrier layer for protecting a substrate member thereunder.

20. The gas sensor assembly of claim 12, further comprising one or more spaced-apart contacts fabricated over a barrier layer, wherein said spaced-apart contacts supports the free-standing gas sensing element.

21. The gas sensor assembly of claim 20, wherein said spaced-apart contacts and said barrier layer form an integral contact/barrier element for supporting the free-standing gas sensing element and isolating same from an underlying substrate.

22. A method of monitoring a fluid locus for the presence of a target gas species therein, said method comprising:
exposing fluid at said fluid locus to a gas sensor assembly as in claim 12;
monitoring said gas sensor assembly; and
responsively generating an output signal when the gas sensor assembly exhibits a response indicative of the presence or change of concentration of the target gas species in said fluid locus.

23. The method of claim 22, wherein the fluid locus comprises an ambient gas environment of a manufacturing process.

24. The method of claim 22, wherein the fluid locus comprises a fluid stream in a semiconductor processing plant.

25. The method of claim 22, wherein the target gas species comprises a fluoro species selected from the group consisting of $NF_3$, $SiF_4$, $C_2F_6$, $HF$, $F_2$, $COF_2$, $ClF_3$, $IF_3$ and activated species thereof.

26. A method of manufacturing a gas sensor assembly comprising a substrate and a free-standing gas sensing element positioned on the substrate and arranged for contact with a gaseous environment susceptible to the presence or change of concentration of one or more target species therein, the free-standing gas sensing element comprising a suspended support structure having at least one protrusion rising above the substrate and a lateral surface contacting the protrusion and extending beyond the protrusion to form an air gap thereunder and wherein at least the lateral surface is coated with a layer of a gas sensing material, and wherein said gas sensing material in exposure to the target gas species exhibits a response indicative of the presence or change of concentration of the target gas species in said gaseous environment; said method comprising the steps of:
depositing on a base structure a first molding material layer;
depositing a second molding material layer on said first molding material layer;
patterning said second molding material layer to form recesses therein that defines a predetermined supporting structure;
depositing a support material in said recesses;
selectively removing the second molding material layer, to form a support structure;
depositing on the support structure a gas sensing material; and
selectively removing the first molding material layer to release the support structure, thereby forming the free-standing gas sensing element comprising the suspended support structure with a layer of gas sensing material coated on at least the lateral surface thereof.

27. The method of claim 26, wherein the first and second molding materials are the same.

28. The method of claim 26, wherein the first and second molding materials are characterized by different removability.

29. The method of claim 26, wherein the support material comprises silicon carbide, wherein the first molding materials comprise silicon dioxide, and wherein the second molding material comprises polysilicon.

30. The method of claim 26, wherein the gas sensing material comprises a transition metal or a noble metal.

31. The method of claim 26, wherein the support material comprises an etch-resistant polymer.

32. The method of claim 26, wherein the gas sensing material comprises Ni or Ni alloy.

33. The method of claim 26, wherein said base structure comprises one or more contacts for supporting the free-standing gas sensing element.

34. The method of claim 33, wherein said one or more contacts are formed of silicon carbide.

35. The method of claim 26, wherein said base structure comprises multiple spaced-apart contacts for supporting the free-standing gas sensing element.

36. A method of manufacturing a gas sensor assembly comprising a substrate and a free-standing gas sensing element positioned on the substrate and arranged for contact with a gaseous environment susceptible to the presence or change of concentration of one or more target gas species therein, the free-standing gas-sensing element comprising a suspended support structure having at least one protrusion rising above the substrate and a lateral surface contacting the protrusion and extending beyond the protrusion to form an air gap thereunder and wherein at least the lateral surface is coated with a layer of a gas sensing material, and wherein said gas sending material in exposure to the target gas species exhibits a response indicative of the presence or change of concentration of the target gas species in said gaseous environment, wherein said free-standing gas sensing element is supported by one or more spaced-apart contacts fabricated over a barrier layer, said method comprising the steps of:

- depositing on the substrate a first molding material layer,
- patterning said first molding material layer to form at least one barrier recess that defines a predetermined barrier structure overlaying the substrate;
- depositing in said barrier recess a barrier material;
- depositing a second molding material layer over the first molding material layer and the barrier material;
- patterning said second molding material layer to provide contact recesses that define one or more predetermined spaced-apart contacts overlaying the barrier material;
- depositing in said contact recesses a contact-forming material;
- depositing a third molding material layer over the second molding material layer and the contact-forming material;
- patterning said third molding material layer to provide support recesses that define a predetermined support structure overlaying both the contact-forming material and the second molding material layer;
- depositing in said support recesses a support material;
- selectively removing the third molding material to form a protruding support structure;
- depositing a gas sensing material on the protruding support structure; and
- selectively removing the first and the second molding materials, thereby forming the free-standing gas sensing element comprising the suspended support structure coated on at least the lateral surface thereof with the layer of gas sensing material,
- wherein such free-standing gas sensing element is supported by such spaced-apart contacts overlaying the barrier layer, and wherein the barrier layer overlays and protects the substrate.

37. A method for forming a free-standing gas sensing element comprising a suspended support structure and a gas sensing layer fanned thereon, comprising the steps of (1) forming said suspended support structure on a substrate in a pattern of at least two spaced apart protruding contacts with a lateral structure spanning between the protruding spaced apart contacts and by using multiple sacrificial molding layers that are subsequently removed to form an air cavity under the lateral structure; and (2) depositing said gas sensing layer over the suspended support structure.

38. A method for forming a free-standing gas sensing element comprising: a substrate; a suspended silicon carbide support structure positioned on the substrate; and a gas sensing metal layer thereon, comprising the steps of (1) forming said suspended silicon carbide support structure by using multiple sacrificial molding layers that are subsequently removed to release said support structure, wherein the support structure comprises at least one protrusion rising above the substrate and a lateral surface supported by the protrusion forming an air gap between the substrate and the lateral surface, wherein said sacrificial molding layers comprises materials selected from the group consisting of silicon dioxide and polysilicon; and (2) depositing said gas sensing metal layer over the suspended silicon carbide support structure.

* * * * *